(12) United States Patent
Bromander et al.

(10) Patent No.: US 8,790,297 B2
(45) Date of Patent: Jul. 29, 2014

(54) REMOTE CATHETER SYSTEM WITH STEERABLE CATHETER

(75) Inventors: Thomas Bromander, Andover, MA (US); Graham Eacock, Westborough, MA (US); John Murphy, North Reading, MA (US); Tal Wenderow, Newton, MA (US)

(73) Assignee: Corindus, Inc., Waltham, MA (US)

( * ) Notice: Subject to any disclaimer, the term of this patent is extended or adjusted under 35 U.S.C. 154(b) by 21 days.

(21) Appl. No.: 13/232,660

(22) Filed: Sep. 14, 2011

(65) Prior Publication Data

US 2012/0179032 A1 Jul. 12, 2012

Related U.S. Application Data

(63) Continuation of application No. PCT/US2010/027666, filed on Mar. 17, 2010.

(60) Provisional application No. 61/161,226, filed on Mar. 18, 2009.

(51) Int. Cl.
*A61M 31/00* (2006.01)

(52) U.S. Cl.
USPC ........................................ 604/95.01; 600/427

(58) Field of Classification Search
None
See application file for complete search history.

(56) References Cited

U.S. PATENT DOCUMENTS

| | | | |
|---|---|---|---|
| 2,718,598 A | 9/1955 | Herbert | |
| 3,147,953 A | 9/1964 | Arth | |
| 3,308,297 A | 3/1967 | Mansker | |
| 4,254,341 A | 3/1981 | Herr et al. | |
| 4,382,184 A | 5/1983 | Wernikoff | |
| 4,581,538 A | 4/1986 | Lenhart | |
| 4,965,456 A | 10/1990 | Huettenrauch et al. | |
| 4,977,588 A | 12/1990 | Van Der | |
| 5,015,864 A | 5/1991 | Maleki | |
| 5,049,147 A | 9/1991 | Danon | |
| 5,090,044 A | 2/1992 | Kobayashi | |

(Continued)

FOREIGN PATENT DOCUMENTS

| | | |
|---|---|---|
| DE | 2856439 A | 7/1980 |
| DE | 4233323 A | 4/1994 |

(Continued)

OTHER PUBLICATIONS

U.S. Appl. No. 29/378,948, Nov. 11, 2010, Murphy.

(Continued)

*Primary Examiner* — Unsu Jung
*Assistant Examiner* — Saurel J Selkin
(74) *Attorney, Agent, or Firm* — Rathe Lindenbaum LLP

(57) ABSTRACT

A catheter procedure system including a user interface for receiving at least a first user input and a second user input and a guide catheter is provided. The catheter procedure system also includes a guide catheter actuating mechanism coupled to the guide catheter and a Y-connector. The guide catheter actuating mechanism is configured to advance and retract the guide catheter in response to the first user input and to rotate the guide catheter in response to the second user input. The catheter procedure system includes a first connector coupling the Y-connector to the guide catheter actuating mechanism, and the first connector is configured to allow the Y-connector to advance and retract with the guide catheter and to allow the guide catheter to rotate without also causing the Y-connector to rotate.

27 Claims, 10 Drawing Sheets

(56) References Cited

U.S. PATENT DOCUMENTS

| | | | |
|---|---|---|---|
| 5,133,364 A * | 7/1992 | Palermo et al. ............... 600/585 |
| 5,139,473 A | 8/1992 | Bradshaw et al. |
| 5,185,778 A | 2/1993 | Magram |
| 5,217,474 A | 6/1993 | Zacca et al. |
| 5,318,541 A | 6/1994 | Viera et al. |
| 5,351,676 A | 10/1994 | Putman |
| 5,377,678 A | 1/1995 | Dumoulin et al. |
| 5,396,880 A | 3/1995 | Kagan et al. |
| 5,423,321 A | 6/1995 | Fontenot |
| 5,425,382 A | 6/1995 | Golden et al. |
| 5,434,775 A | 7/1995 | Sims et al. |
| 5,464,023 A | 11/1995 | Viera |
| 5,484,407 A | 1/1996 | Osypka |
| 5,487,734 A | 1/1996 | Thorne et al. |
| 5,492,131 A | 2/1996 | Galel |
| 5,524,180 A | 6/1996 | Wang et al. |
| 5,540,649 A | 7/1996 | Bonnell et al. |
| 5,578,014 A * | 11/1996 | Erez et al. ............... 604/192 |
| 5,584,078 A | 12/1996 | Saboory |
| 5,586,968 A | 12/1996 | Gruendl et al. |
| 5,623,943 A | 4/1997 | Hackett et al. |
| 5,644,613 A | 7/1997 | Mick |
| 5,654,864 A | 8/1997 | Ritter et al. |
| 5,690,645 A | 11/1997 | Van Erp |
| 5,697,377 A | 12/1997 | Wittkampf |
| 5,704,897 A | 1/1998 | Truppe |
| 5,706,827 A | 1/1998 | Ehr et al. |
| 5,728,044 A | 3/1998 | Shan |
| 5,741,271 A | 4/1998 | Nakao et al. |
| 5,779,623 A | 7/1998 | Bonnell |
| 5,821,920 A | 10/1998 | Rosenberg et al. |
| 5,842,987 A | 12/1998 | Sahadevan |
| 5,851,182 A | 12/1998 | Sahadevan |
| 5,882,333 A * | 3/1999 | Schaer et al. ............... 604/95.01 |
| 5,957,941 A | 9/1999 | Ream |
| 5,981,964 A | 11/1999 | Mcauley et al. |
| 6,004,276 A | 12/1999 | Wright et al. |
| 6,013,038 A | 1/2000 | Pflueger |
| 6,024,749 A | 2/2000 | Shturman et al. |
| 6,048,300 A | 4/2000 | Thornton et al. |
| 6,083,170 A | 7/2000 | Ben-Haim |
| 6,096,004 A | 8/2000 | Meglan et al. |
| 6,126,647 A | 10/2000 | Posey et al. |
| 6,171,234 B1 | 1/2001 | White et al. |
| 6,233,476 B1 | 5/2001 | Strommer et al. |
| 6,258,052 B1 | 7/2001 | Milo |
| 6,261,247 B1 | 7/2001 | Ishikawa et al. |
| 6,266,552 B1 | 7/2001 | Slettenmark |
| 6,285,898 B1 | 9/2001 | Ben-Haim |
| 6,290,675 B1 | 9/2001 | Vujanic et al. |
| 6,351,513 B1 | 2/2002 | Bani-Hashemi et al. |
| 6,358,199 B1 | 3/2002 | Pauker et al. |
| 6,375,471 B1 | 4/2002 | Wendlandt et al. |
| 6,447,504 B1 | 9/2002 | Ben-Haim et al. |
| 6,448,571 B1 | 9/2002 | Goldstein |
| 6,497,444 B1 | 12/2002 | Simon |
| 6,499,163 B1 | 12/2002 | Stensby |
| 6,522,909 B1 | 2/2003 | Garibaldi et al. |
| 6,540,670 B1 | 4/2003 | Hirata et al. |
| 6,554,472 B1 | 4/2003 | Dietz et al. |
| 6,610,007 B2 | 8/2003 | Belson et al. |
| 6,653,648 B2 | 11/2003 | Goldstein |
| 6,705,990 B1 | 3/2004 | Gallant et al. |
| 6,726,675 B1 * | 4/2004 | Beyar ............... 604/510 |
| 6,740,103 B2 | 5/2004 | Hall et al. |
| 6,770,066 B1 | 8/2004 | Weaver et al. |
| 6,835,173 B2 | 12/2004 | Couvillon, Jr. |
| 6,878,106 B1 | 4/2005 | Herrmann |
| 6,997,870 B2 | 2/2006 | Couvillon, Jr. |
| 7,087,013 B2 | 8/2006 | Belson et al. |
| 7,112,811 B2 | 9/2006 | Lemer |
| 7,276,044 B2 | 10/2007 | Ferry et al. |
| 7,294,135 B2 | 11/2007 | Stephens et al. |
| 7,608,847 B2 | 10/2009 | Rees |
| 7,615,032 B2 | 11/2009 | Whittaker et al. |
| 7,615,042 B2 | 11/2009 | Beyar et al. |
| 7,632,265 B2 | 12/2009 | Hauck et al. |
| 7,663,128 B2 | 2/2010 | Arterson |
| 7,666,135 B2 | 2/2010 | Couvillon, Jr. |
| 7,686,816 B2 | 3/2010 | Belef et al. |
| 7,697,972 B2 | 4/2010 | Verard et al. |
| 7,706,894 B2 | 4/2010 | Stewart et al. |
| 7,729,743 B2 | 6/2010 | Sabczynski et al. |
| 7,766,894 B2 | 8/2010 | Weitzner et al. |
| 7,769,427 B2 | 8/2010 | Shachar |
| D626,250 S | 10/2010 | Wenderow et al. |
| 7,811,294 B2 | 10/2010 | Strommer et al. |
| 7,848,788 B2 | 12/2010 | Tulley et al. |
| 7,887,549 B2 | 2/2011 | Wenderow et al. |
| 7,905,853 B2 | 3/2011 | Chapman et al. |
| 7,967,773 B2 | 6/2011 | Amborn et al. |
| 7,984,659 B2 | 7/2011 | Fujimoto et al. |
| 8,043,362 B2 | 10/2011 | Gong et al. |
| 8,046,049 B2 | 10/2011 | Govari et al. |
| 8,187,229 B2 | 5/2012 | Weitzner et al. |
| 8,257,302 B2 | 9/2012 | Beyar et al. |
| 8,343,096 B2 | 1/2013 | Kirschenman et al. |
| 8,390,438 B2 | 3/2013 | Olson et al. |
| 2001/0025142 A1 | 9/2001 | Wessels et al. |
| 2002/0087166 A1 | 7/2002 | Brock et al. |
| 2002/0109107 A1 | 8/2002 | Goldstein |
| 2002/0115931 A1 | 8/2002 | Strauss et al. |
| 2002/0168618 A1 | 11/2002 | Anderson et al. |
| 2002/0177789 A1 | 11/2002 | Ferry et al. |
| 2003/0036712 A1 | 2/2003 | Heh et al. |
| 2003/0040671 A1 | 2/2003 | Somogyi et al. |
| 2003/0069719 A1 | 4/2003 | Cunningham et al. |
| 2003/0078003 A1 | 4/2003 | Hunter et al. |
| 2003/0088209 A1 | 5/2003 | Chiu et al. |
| 2003/0176770 A1 | 9/2003 | Merril et al. |
| 2003/0199848 A1 | 10/2003 | Ledesma et al. |
| 2003/0210259 A1 | 11/2003 | Liu et al. |
| 2004/0015974 A1 | 1/2004 | Jeyaraman |
| 2004/0044279 A1 | 3/2004 | Lewin et al. |
| 2004/0064086 A1 * | 4/2004 | Gottlieb et al. ............... 604/43 |
| 2004/0068173 A1 * | 4/2004 | Viswanathan ............... 600/407 |
| 2004/0085294 A1 | 5/2004 | Michelitsch et al. |
| 2004/0113498 A1 | 6/2004 | Kroenke |
| 2004/0138548 A1 | 7/2004 | Strommer et al. |
| 2004/0152974 A1 | 8/2004 | Solomon |
| 2004/0254566 A1 | 12/2004 | Plicchi et al. |
| 2005/0008210 A1 | 1/2005 | Evron et al. |
| 2005/0107697 A1 | 5/2005 | Berke |
| 2005/0119615 A1 | 6/2005 | Noriega et al. |
| 2005/0203382 A1 | 9/2005 | Govari et al. |
| 2005/0222554 A1 * | 10/2005 | Wallace et al. ............... 606/1 |
| 2005/0245846 A1 | 11/2005 | Casey |
| 2005/0256504 A1 | 11/2005 | Long et al. |
| 2005/0273199 A1 | 12/2005 | Ban et al. |
| 2005/0277851 A1 | 12/2005 | Whittaker et al. |
| 2005/0283075 A1 | 12/2005 | Ma et al. |
| 2006/0041181 A1 | 2/2006 | Viswanathan et al. |
| 2006/0041245 A1 | 2/2006 | Ferry et al. |
| 2006/0066574 A1 | 3/2006 | Kim et al. |
| 2006/0074442 A1 | 4/2006 | Noriega et al. |
| 2006/0084911 A1 | 4/2006 | Belef et al. |
| 2006/0116575 A1 | 6/2006 | Willis |
| 2006/0146010 A1 | 7/2006 | Schneider |
| 2006/0186061 A1 | 8/2006 | Briggs et al. |
| 2006/0229587 A1 | 10/2006 | Beyar et al. |
| 2006/0258935 A1 | 11/2006 | Pile-Spellman et al. |
| 2006/0282140 A1 | 12/2006 | Schock et al. |
| 2007/0016029 A1 | 1/2007 | Donaldson et al. |
| 2007/0043338 A1 | 2/2007 | Moll et al. |
| 2007/0060879 A1 | 3/2007 | Weitzner et al. |
| 2007/0083193 A1 | 4/2007 | Werneth et al. |
| 2007/0103437 A1 | 5/2007 | Rosenberg |
| 2007/0106247 A1 | 5/2007 | Burnett et al. |
| 2007/0118079 A1 | 5/2007 | Moberg et al. |
| 2007/0123070 A1 | 5/2007 | Bencteux |
| 2007/0142749 A1 | 6/2007 | Khatib et al. |
| 2007/0185480 A1 | 8/2007 | El-Galley et al. |
| 2007/0185486 A1 | 8/2007 | Hauck et al. |
| 2007/0197896 A1 | 8/2007 | Moll et al. |

(56) References Cited

U.S. PATENT DOCUMENTS

| | | | |
|---|---|---|---|
| 2007/0239106 A1* | 10/2007 | Weitzner et al. | 604/95.01 |
| 2007/0250097 A1 | 10/2007 | Weitzner et al. | |
| 2007/0276216 A1 | 11/2007 | Beyar et al. | |
| 2007/0276234 A1 | 11/2007 | Shahidi | |
| 2008/0000485 A1 | 1/2008 | Williams et al. | |
| 2008/0027313 A1 | 1/2008 | Shachar | |
| 2008/0051820 A1* | 2/2008 | Gong et al. | 606/191 |
| 2008/0059598 A1 | 3/2008 | Garibaldi et al. | |
| 2008/0097224 A1 | 4/2008 | Murphy et al. | |
| 2008/0146922 A1 | 6/2008 | Steins et al. | |
| 2008/0161801 A1 | 7/2008 | Steinke et al. | |
| 2008/0167750 A1 | 7/2008 | Stahler et al. | |
| 2008/0217564 A1 | 9/2008 | Beyar et al. | |
| 2008/0221922 A1 | 9/2008 | Putnam et al. | |
| 2008/0221992 A1 | 9/2008 | Bernstein | |
| 2008/0249536 A1 | 10/2008 | Stahler et al. | |
| 2008/0269663 A1 | 10/2008 | Arnold et al. | |
| 2009/0012533 A1 | 1/2009 | Barbagli et al. | |
| 2009/0105639 A1 | 4/2009 | Weitzner et al. | |
| 2009/0110152 A1 | 4/2009 | Manzke et al. | |
| 2009/0131955 A1 | 5/2009 | Wenderow et al. | |
| 2009/0137952 A1 | 5/2009 | Ramamurthy et al. | |
| 2009/0138025 A1 | 5/2009 | Stahler et al. | |
| 2009/0221958 A1 | 9/2009 | Beyar et al. | |
| 2009/0247933 A1 | 10/2009 | Maor et al. | |
| 2009/0247944 A1 | 10/2009 | Kirschenman et al. | |
| 2009/0247993 A1* | 10/2009 | Kirschenman et al. | 606/1 |
| 2010/0069833 A1 | 3/2010 | Wenderow et al. | |
| 2010/0073150 A1 | 3/2010 | Olson et al. | |
| 2010/0076308 A1 | 3/2010 | Wenderow et al. | |
| 2010/0076309 A1 | 3/2010 | Wenderow et al. | |
| 2010/0076310 A1 | 3/2010 | Wenderow et al. | |
| 2010/0084586 A1 | 4/2010 | Teodorescu | |
| 2010/0130987 A1 | 5/2010 | Wenderow et al. | |
| 2010/0175701 A1 | 7/2010 | Reis et al. | |
| 2010/0292651 A1 | 11/2010 | Yodfat et al. | |
| 2010/0318100 A1 | 12/2010 | Okamoto et al. | |
| 2011/0004144 A1 | 1/2011 | Beiriger et al. | |
| 2011/0015569 A1 | 1/2011 | Kirschenman et al. | |
| 2011/0109283 A1 | 5/2011 | Kapels et al. | |
| 2011/0144658 A1 | 6/2011 | Wenderow et al. | |
| 2011/0152882 A1 | 6/2011 | Wenderow et al. | |
| 2012/0179032 A1* | 7/2012 | Bromander et al. | 600/434 |

FOREIGN PATENT DOCUMENTS

| | | |
|---|---|---|
| EP | 0329492 A | 8/1989 |
| EP | 0331944 A | 9/1989 |
| EP | 0554986 A | 8/1993 |
| EP | 0590268 A | 4/1994 |
| EP | 0970663 A | 1/2000 |
| EP | 1415660 A | 5/2004 |
| EP | 1442720 A | 8/2004 |
| EP | 1504713 A | 2/2005 |
| EP | 1554986 A | 7/2005 |
| EP | 1792638 A | 6/2007 |
| FR | 2167098 A | 8/1973 |
| JP | 07184923 | 7/1995 |
| JP | 7328016 | 12/1995 |
| SU | 279814 A | 7/1975 |
| SU | 992067 A | 1/1983 |
| WO | 9320876 A | 10/1993 |
| WO | 9502233 A | 1/1995 |
| WO | 9621486 A | 7/1996 |
| WO | 0174252 A | 10/2001 |
| WO | 0209571 A | 2/2002 |
| WO | 02064011 A | 8/2002 |
| WO | 2005000105 A | 1/2005 |
| WO | 2006018841 A | 2/2006 |
| WO | 2006120666 A | 11/2006 |
| WO | 2007036925 A | 4/2007 |
| WO | 2009137410 A | 11/2009 |
| WO | 2010025336 A | 3/2010 |
| WO | 2010025338 A | 3/2010 |
| WO | 2010068783 A | 6/2010 |
| WO | 2010107916 A | 9/2010 |
| WO | 2011046874 A | 4/2011 |

OTHER PUBLICATIONS

Anderson, J., Chui, C.K., Cai. Y., Wang Y., Eng, Z.L.M., Eng, X.M. M., Nowinski, W., Solaiyappan, M., Murphy, K., Gailloud, P. & Venbrux, A., Virtual Reality Training in International Radiology: The John Hopkins and Kent Ridge Digital Labratory Experience, Theime Medical Publishers, 2002, 2 pages, vol. 19, No. 2, New York, NY.

Becker, Y, Cancer in ataxia-telangiectasia patients: Analysis of factors leading to radiation-induced and spontaneous tumors, Anticancer Res., 1986, vol. 6, No. 5, Abstract, pp. 1021-1032, Israel.

Beyar, R., Gruberg, L., Deleanu, D., Roguin, A., Almagor, Y., Cohen, S., Kumar, G., & Wenderow, T., Remote Control Percutaneous Coronary Interventions, Journal of American College of Cardiology, 2006, vol. 47, No. 2, 5 pages, Elsevier Inc., Haifa, Israel.

Biazzi, L. & Garbagna, P., Exposition Aux Radiations Et Protection Pendant Les Examens Angiographiques, Ann. Radiol., 1979, vol. 22, No. 4, Abstract, pp. 345-347, France.

Essinger A., Raimondi, S. & Valley, J.F., Radiation Exposure to the Examiner During Coronary Angiography, Ann. Radiol., 1979 vol. 22 No. 4 Abstract, pp. 340-343, France.

Favaretti, C., Stritoni, P., Mariotti, A., Bressan, M. & Razzolini, R., The Distribution and Activities of Hemodynamic Laboratories in Italy: The implications for the Quality of Services, G Ital Cardiol, May 1994, vol. 24 No. 5, Abstract, pp. 477-482, Italy.

Magnavita, N. & Fileni, A., Occupational risk caused by ultrasound in medicine, Radiologica Medica, Jul.-Aug. 1994, vol. 88, No. 1-2, Abstract, pp. 107-111, Italy.

Roach, H., Larson, E., Cobran, T. & Bartlett, B., Intravenous site care practices in critical care: a national survey, Heart Lung, Sep.-Oct. 1995, vol. 24, No. 5, Abstract, pp. 420-424, Washington D.C., United States.

Van Den Brand, M., Utilization or coronary angioplasty and cost or angioplasty disposables in 14 western European countries, Europe Heart Journal, Mar. 1993, vol. 14, No. 3, Abstract, pp. 391-397, Rotterdam, Netherlands.

Wu, J.R., Huang, T.Y., Wu, D.K., Hsu, P.C. & Weng, P.S., An investigation of radiation exposure on pediatric patients and doctors during cardiac catheterization and cineangiography, Journal of Medical Sciences, Sep. 1991, vol. 7, No. 9, Abstract, pp. 448-453, Taiwan, China.

Machine Translation of Patent FR 2,167,098.
Machine Translation of Patent JP 7,184,923.
Machine Translation of Patent JP 7,32,8016.
Machine Translation of Patent De 4,23,323.

* cited by examiner

REMOTE CATHETER SYSTEM WITH STEERABLE CATHETER

CROSS-REFERENCE TO RELATED PATENT APPLICATION

This application is a Continuation of U.S. Application No. PCT/US10/27666 titled "Remote Catheter System with Steerable Catheter" filed on Mar. 17, 2010, which claims the benefit of priority to U.S. Provisional Application No. 61/161,226, filed Mar. 18, 2009, which are both incorporated herein by reference in their entirety.

BACKGROUND OF THE INVENTION

The present invention relates generally to the field of catheter systems for performing diagnostic and/or intervention procedures. The present invention relates specifically to catheter systems including a moveable, steerable or deflectable guide catheter.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases may be treated with catheterization procedures.

SUMMARY OF THE INVENTION

One embodiment of the invention relates to a catheter procedure system including a user interface for receiving at least a first user input and a second user input and a guide catheter. The catheter procedure system also includes a guide catheter actuating mechanism coupled to the guide catheter and a Y-connector. The guide catheter actuating mechanism is configured to advance and retract the guide catheter in response to the first user input and to rotate the guide catheter in response to the second user input. The catheter procedure system includes a first connector coupling the Y-connector to the guide catheter actuating mechanism, and the first connector is configured to allow the Y-connector to advance and retract with the guide catheter and to allow the guide catheter to rotate without also causing the Y-connector to rotate.

Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
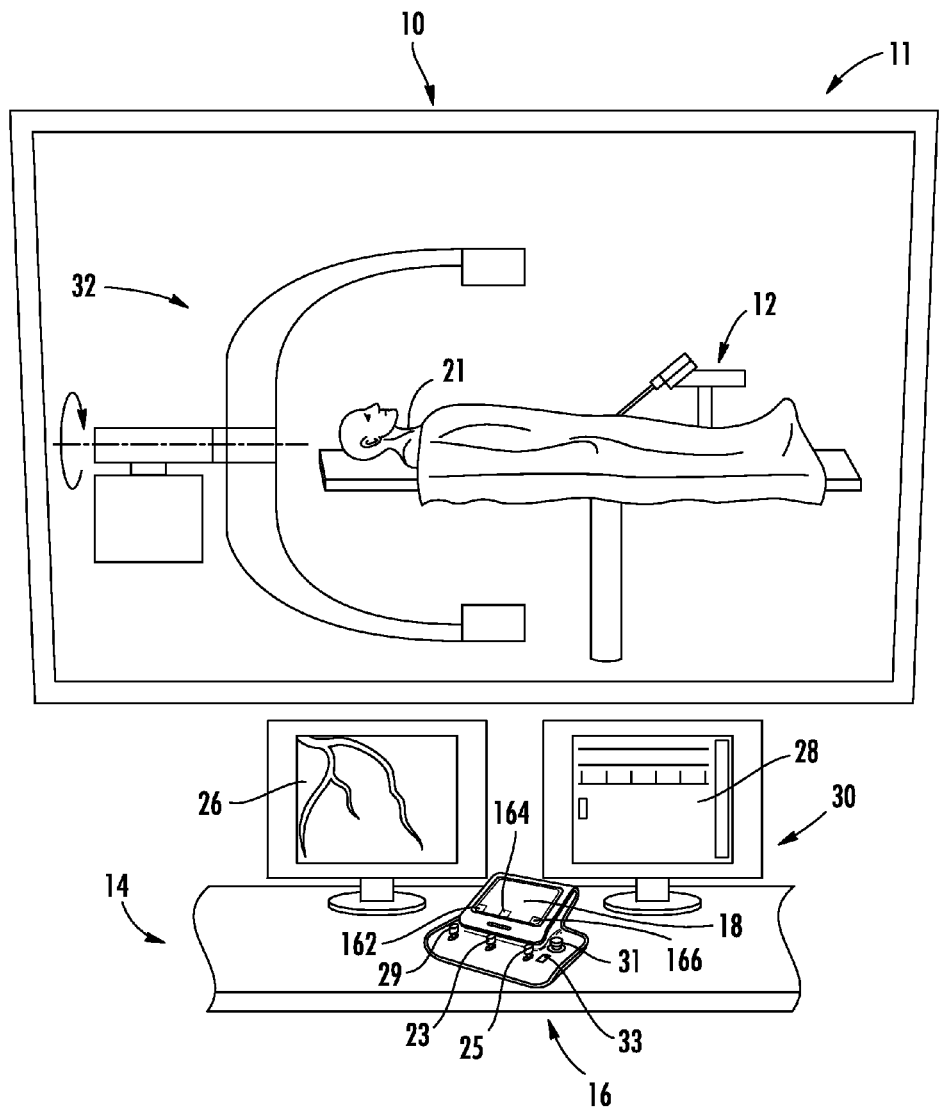
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., angioplasty, stent placement, treatment of peripheral vascular disease, etc.) during which a catheter is used to treat a disease. It should be noted, however, that one skilled in the art would recognize that, certain specific percutaneous intervention devices or components (e.g., type of guide wire, type of catheter, etc.) will be selected based on the type of procedure that is to be preformed. Catheter procedure system 10 is capable of performing any number of catheter based medical procedures with minor adjustments to accommodate the specific percutaneous intervention devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, shown as bedside system 12, located within lab unit 11 adjacent patient 21. Generally, bedside system 12 may be equipped with the appropriate percutaneous intervention devices or other components (e.g., guide wires, guide catheters, working catheters, catheter balloons, stents, contrast media, medicine, diagnostic catheters, etc.) to allow the user to perform a catheter based medical procedure. A robotic catheter system, such as bedside system 12, may be any system configured to allow a user to perform a catheter-based medical procedure via a robotic system by operating various controls such as the controls located at workstation 14. Bedside system 12 may include any number and/or combination of components to provide bedside system 12 with the functionality described herein. Various embodiments of bedside system 12 are described in detail in International Application No. PCT/US2009/042720, filed May 4, 2009, which is incorporated herein by reference in its entirety.

In one embodiment, bedside system 12 is equipped with a steerable (e.g., guidable, deflectable, bendable, etc.) guide catheter that is configured to allow a user to control bending of the distal tip of the guide catheter via manipulation of controls located at workstation 14. In one embodiment, bedside system 12 may be used to perform a catheter based diagnostic procedure. In this embodiment, bedside system 12 may be equipped with a steerable guide catheter for the delivery of contrast media to the coronary arteries. During such a procedure, the user may bend the distal tip of the steerable guide catheter to deliver contrast media to the coronary arteries on the left side of the heart, to deliver contrast media to the coronary arteries on the right side of the heart, and/or to deliver contrast media into the chambers of the heart as desired.

In another embodiment, bedside system 12 may be equipped to perform a catheter based therapeutic procedure. In this embodiment, bedside system 12 may be equipped with a steerable guide catheter, a guide wire, and a working catheter (e.g., a balloon catheter, a stent delivery catheter, etc.). During a therapeutic procedure, the user may bend the distal tip of the steerable guide catheter to position the distal tip of the guide catheter as desired by the user. In addition, the user may bend the distal tip of the steerable guide catheter to navigate the guide catheter around bends and curves in a patient's vascular system. In another embodiment, any of the percutaneous intervention devices of bedside system 12 may be equipped with positional sensors that indicate the position of the component within the body or the position of percutaneous device relative to each other.

Bedside system 12 is in communication with workstation 14, allowing signals generated by the user inputs of workstation 14 to be transmitted to bedside system 12 to control the various functions of beside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 is capable of being remotely located, for example, in either a procedure room or a separate control room. Workstation 14 may be located at any place within a hospital. Workstation 14 may also be in any location outside of the hospital, such as in a physician's offsite office, mobile workstation trailer, etc. If workstation 14 is located such that the user is not able to directly view patient 21 within lab unit 11, lab unit 11 may be equipped with a camera to allow the user located at workstation 14 to see the patient within lab unit 11. If imaging system 32 is a radiation based imaging device, remotely locating workstation 14 enables users to perform procedures outside the radiation zone created by imaging system 32. In addition, remotely locating workstation 14 may allow users to multitask outside the procedure room during downtime.

Workstation 14 includes a user interface 30. User interface 30 includes controls 16. Controls 16 allow the user to control bedside system 12 to perform a catheter based medical procedure. For example, controls 16 may be configured to cause bedside system 12 to perform various tasks using the various percutaneous intervention devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). In addition, controls 16 may also be configured to allow the user located at remote workstation 14 to control the bending of the distal tip of a steerable guide catheter.

In one embodiment, controls 16 include a touch screen 18, a dedicated guide catheter control 29, a dedicated guide wire control 23, and a dedicated working catheter control 25. In this embodiment, guide wire control 23 is a joystick configured to advance, retract, or rotate a guide wire, working catheter control 25 is a joystick configured to advance, refract, or rotate a working catheter, and guide catheter control 29 is a joystick configured to advance, retract, or rotate a guide catheter. Guide catheter control 29 may also be configured to allow the user to bend the distal tip of a steerable guide catheter. In one embodiment, controls 16 may include one or more controls or icons displayed on touch screen 18, that, when activated, causes the distal tip of the steerable guide catheter to bend to a particular angle or to bend to a particular shape. For example, touch screen 18 may include several icons (such as icons 162, 164, or 166) each indicating a different bend angle or bend shape (e.g., a button for a 30 degree bend, a button for a 40 degree bend, a button for the Judkins Left 4 bend, a button for the Judkins Right 4 bend, etc.), and when the user pushes the button for a particular degree bend or bend shape, the distal tip of the guide catheter is controlled to bend to the bend angle or bend shape associated with the button. In one embodiment, the user may select or assign particular bend angles or bend shapes to the icons of touch screen 18 as desired by the user.

Controls 16 may also include a balloon or stent control that is configured to inflate or deflate a balloon and/or a stent. Each of the controls may include one or more buttons, joysticks, touch screens, etc. that may be desirable to control the particular component to which the control is dedicated. In addition, touch screen 18 may display one or more icons, such as icons 162, 164, 166, related to various portions of controls 16 or to various components of catheter procedure system 10.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 26 and second monitor 28 may be configured to display procedure specific information (e.g., duration of procedure, catheter or guide wire position, volume of medicine or contrast agent delivered, etc.). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MRI, ultrasound, etc.). In an exemplary embodiment, imaging system 32 is a digital x-ray imaging device that is in communication with workstation 14. As shown in FIG. 1, imaging system 32 may include a C-arm that allows imaging system 32 to partially or completely rotate around patient 21 in order to obtain images at different angular positions relative to patient 21 (e.g., sagital views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, stent, etc. during the procedure. The image or images may be displayed on first monitor 26 and/or second monitor 28. In particular, images may be displayed on first monitor 26 and/or second monitor 28 to allow the user to accurately steer or bend the distal tip of a steerable guide catheter into the proper position.

In addition, the user of workstation 14 may be able to control the angular position of imaging system 32 relative to the patient to obtain and display various views of the patient's heart on first monitor 26 and/or second monitor 28. Displaying different views at different portions of the procedure may aid the user of workstation 14 to properly move and position the percutaneous intervention devices within the 3D geometry of the patient's heart. For example, displaying the proper view during a procedure may allow the user to view a patient's vascular system from the proper angle to ensure that the distal tip of a steerable guide catheter is bent in the proper way to ensure the catheter is moved as intended. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 16 may also be configured to allow the user positioned at workstation 14 to control various functions of imaging system 32 (e.g., image capture, magnification, collimation, c-arm positioning, etc.).

Figure 2:
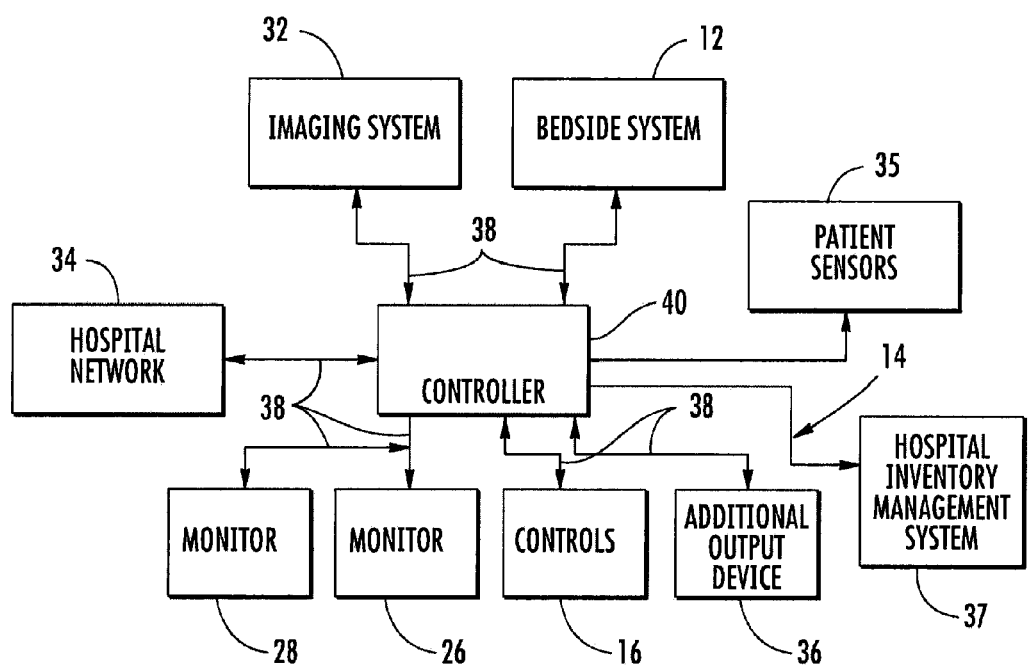
FIG. 2 is block diagram of a catheter procedure system according to an exemplary embodiment.

Referring to FIG. 2, a block diagram of catheter procedure system 10 is shown according to an exemplary embodiment. Catheter procedure system 10 may include a control system, shown as controller 40. Controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34, one or more additional output devices 36 (e.g., printer, disk drive, cd/dvd writer, etc.), and a hospital inventory management system 37.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, contrast media and/or medicine injection systems, medicine tracking and/or logging systems, user logs, encryption systems, systems to restrict access or use of catheter procedure system 10, robotic catheter systems of the past, present, or future, etc.

Figure 3A:
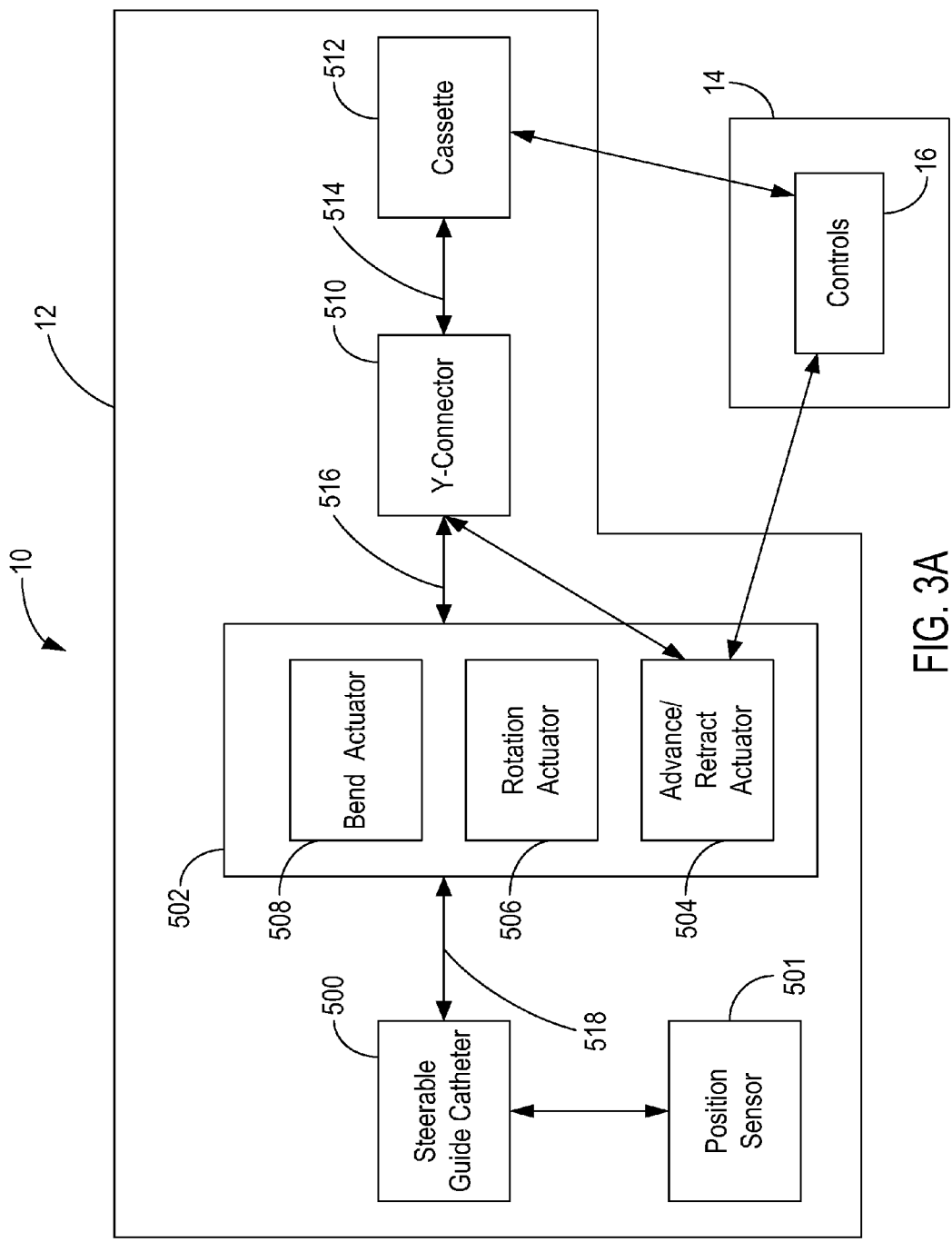
FIG. 3A is a block diagram of a catheter procedure system including a steerable guide catheter and guide catheter actuator according to an exemplary embodiment.

Referring to FIG. 3A, a block diagram of an embodiment of catheter procedure system 10 configured to be equipped with a steerable guide catheter 500 is shown. As discussed above, steerable guide catheter 500 is a guide catheter that allows the user to control bending or deflection of the distal tip of the guide catheter. Steerable guide catheter 500 is coupled to a guide catheter actuating mechanism 502 that moves steerable guide catheter 500 in response to a user's manipulation of controls 16. Steerable guide catheter 500 is coupled to a guide catheter actuating mechanism 502 via connector 518. In various embodiments, connector 518 may be a component separate from both guide catheter 500 and from guide catheter actuating mechanism 502. In other embodiments, connector 518 may be part of guide catheter 500 or part of (e.g., integral with) actuating mechanism 502. Guide catheter actuating mechanism 502 includes an advance/retract actuator 504, a rotation actuator 506, and a bend actuator 508.

Figure 3B:
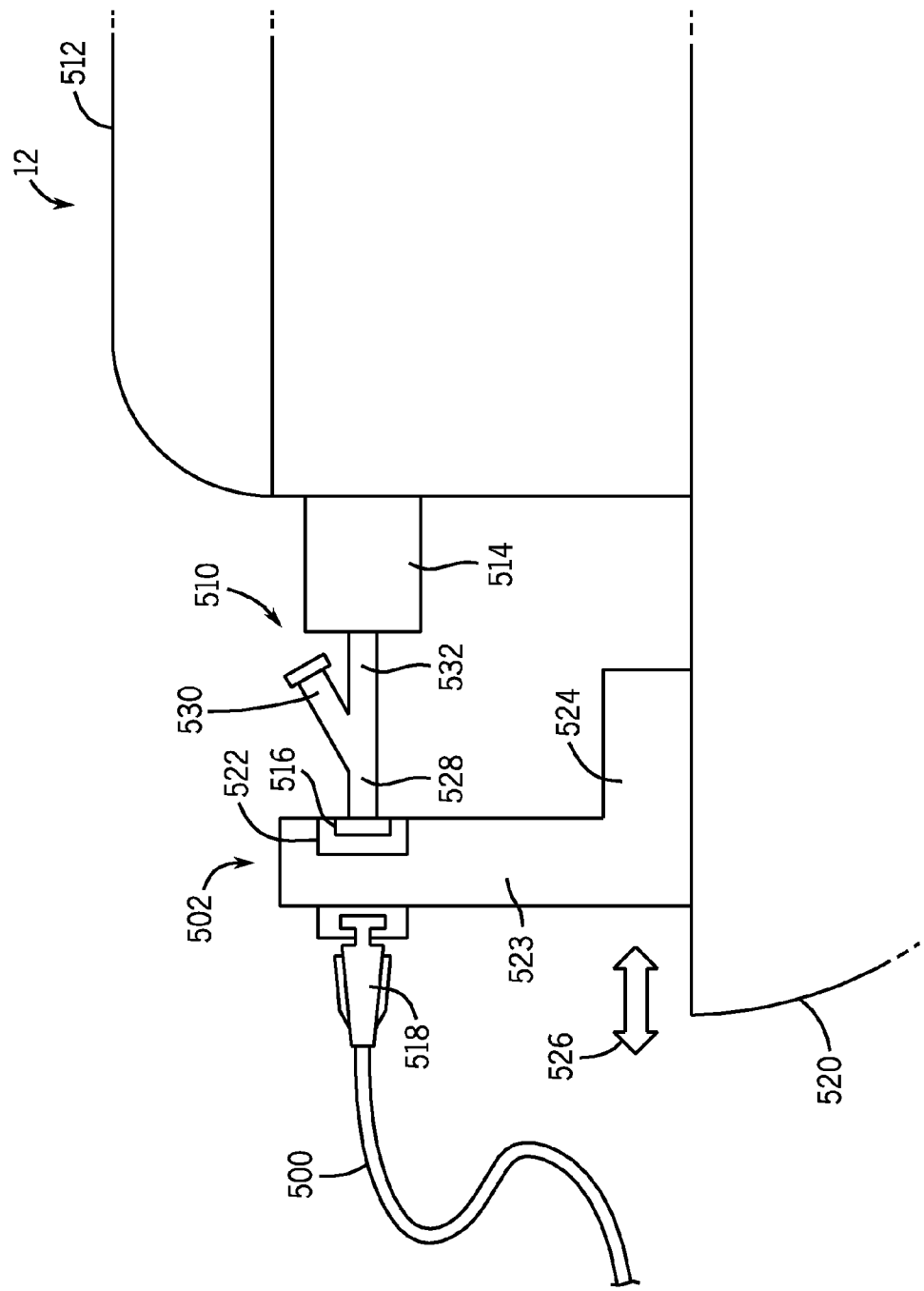
FIG. 3B is a side view of a bedside system including a steerable guide catheter and guide catheter actuator according to an exemplary embodiment.

A Y-connector 510 is coupled to guide catheter actuating mechanism 502 via connector 516. In various embodiments, connector 516 may be a component separate from both Y-connector 510 and guide catheter actuating mechanism 502. In other embodiments, connector 516 may be part of (e.g., integral with) Y-connector 510 or part of actuating mechanism 502 (as shown in FIG. 3B).

Y-connector 510 is also coupled to guide catheter 500. As shown in FIG. 3B, the Y-connector 510 includes three legs, a first leg 528, a second leg 530, and a third leg 532. Each of the legs of Y-connector 510 includes an internal lumen that provides for communication between the various percutaneous devices as discussed herein. First leg 528 of Y-connector 510 is connected to or in communication with the internal lumen of guide catheter 500. In one embodiment, first leg 528 of the Y-connector includes a tube that is connected manually to the internal lumen of guide catheter 500. Second leg 530 is angled away from the longitudinal axis of guide catheter 500 and is in communication with the lumen of first leg 528. Second leg 530 provides a port for the injection of fluids (e.g., contrast media, medicine, etc.) into the lumen of guide catheter 500. Third leg 532 of Y-connector 510 is coupled to a cassette 512 via connector 514. In one embodiment, connector 514 is part of cassette 512. Third leg 532 is in communication with the lumen of first leg 528 such that percutaneous devices of cassette 512 may be advanced into guide catheter 500 through Y-connector 510.

Cassette 512 includes various percutaneous devices (guide wire, working catheter, etc.) and various actuating elements (e.g., a guide wire actuator, a working catheter actuator, etc.) that allows the user to control movement of the percutaneous devices of cassette 512 via operation of controls 16. Cassette 512 may be mounted onto a motor drive base 520 (shown in FIG. 3B) that provides power to the various actuating elements, and, in some embodiments, motor drive base 520 is coupled to an articulating arm positioned near patient 21. Various embodiments of bedside system 12 and cassette 512 is described in detail in International Application No. PCT/US2009/042720, filed May 4, 2009, which is incorporated herein by reference in its entirety. The percutaneous devices of cassette 512 can be moved into the lumen of guide catheter 500 by passing through connector 514 into third leg 532 of Y-connector 510 then into first leg 528 of Y-connector 510. In this embodiment, connector 516, guide catheter actuator 502, and connector 518 also define a path or channel allowing communication between a lumen of guide catheter 500 and first leg 528 of Y-connector 510 such that the percutaneous devices of cassette 512 may be advanced from cassette 512 into guide catheter 500.

In one embodiment, guide catheter actuating mechanism 502 is incorporated in cassette 512. In one embodiment, Y-connector 510 may be moved (e.g., rotated, tilted, etc.) relative to cassette 512 to facilitate insertion of the percutaneous devices of cassette 512 into third leg 532 of Y-connector 510. For example, in one embodiment, Y-connector 510 is moveable between a first, tilted position and a second, untilted position. In this embodiment, the guide wire and/or working catheter is inserted into Y-connector 510 after the Y-connector is moved to the tilted position.

As shown in the block diagram of FIG. 3A, controls 16 located at workstation 14 are communicably coupled to various portions of bedside system 12 to allow the user to control movement of steerable guide catheter 500 and other percutaneous devices that bedside system 12 is equipped with. In the embodiment shown, controls 16 are coupled to guide catheter actuating mechanism 502 to allow the user to move guide catheter 500. In addition, controls 16 are coupled to cassette 512 to allow the user to control the percutaneous devices of cassette 512.

Advance/retract actuator 504 is configured to advance and/or retract steerable guide catheter 500 (i.e., to advance and/or retract along the longitudinal axis of the guide catheter) within patient 21. Rotation actuator 506 is configured to cause rotation of guide catheter 500 about its longitudinal axis. Bend actuator 508 is configured to cause the distal tip of guide catheter 500 to bend. In one embodiment, Y-connector 510 is coupled to guide catheter actuating mechanism 502 such that when guide catheter 500 is advanced or retracted, Y-connector 510 advances or retracts along with guide catheter 500.

Figure 3C:
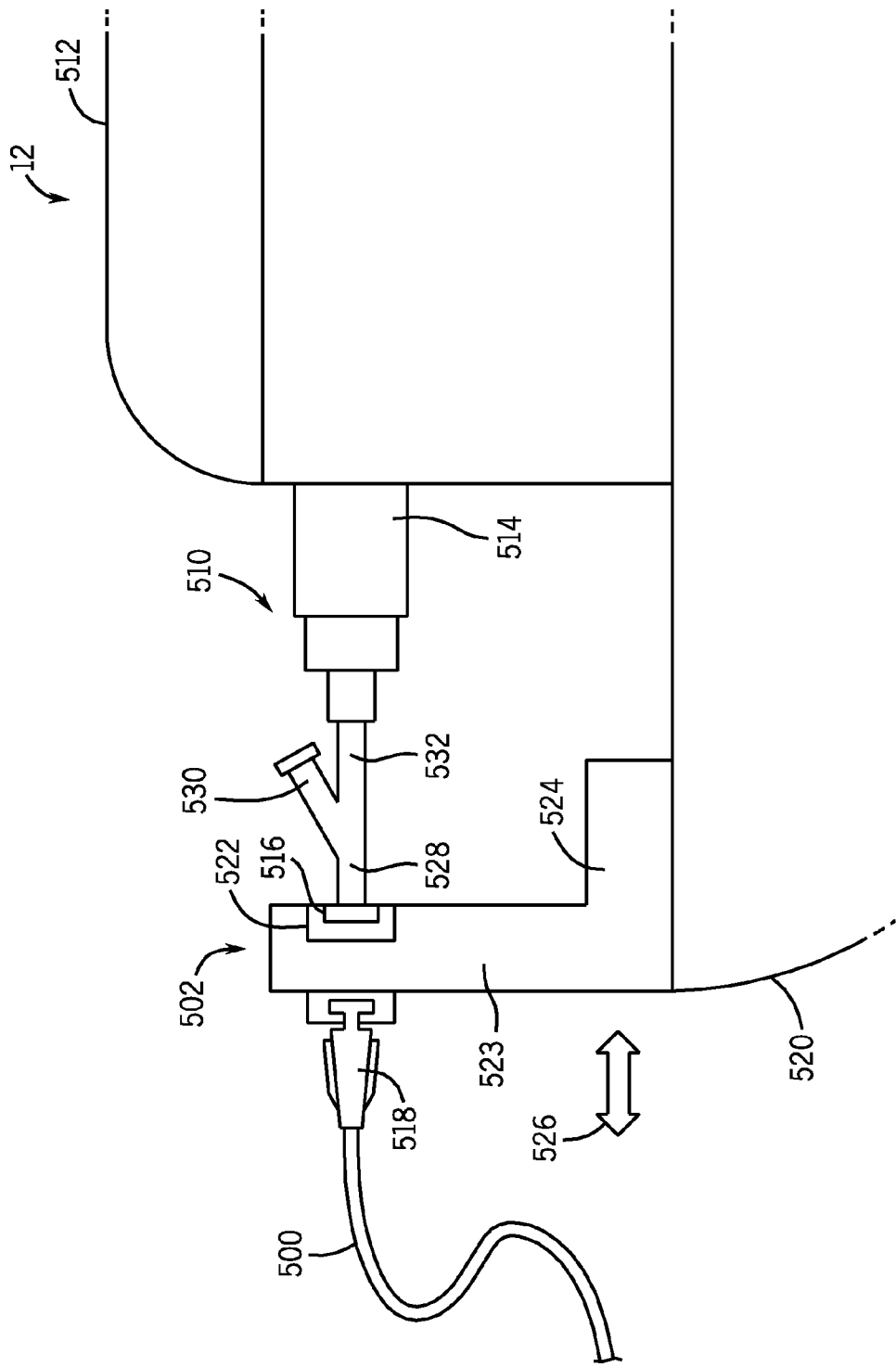
FIG. 3C is a side view of the bedside system of FIG. 3B showing the guide catheter actuator and y-connector after advancement of the guide catheter.

Referring to FIG. 3B and FIG. 3C, one embodiment of the bedside system 12 of FIG. 3A is shown having a steerable guide catheter 500, Y-connector 510, and a cassette 512, according to an exemplary embodiment. As shown in FIG. 3B, Y-connector 510 includes a first leg 528, a second leg 530, and a third leg 532. Guide catheter actuating mechanism 502 is shown including a Y-connector rotational actuator 522 and a moveable base 524. Y-connector rotational actuator 522 allows the user to rotate Y-connector 510 relative to guide catheter actuating mechanism 502 in response to manipulation of controls 16 by the user.

Moveable base 524 is moveably coupled to motor drive base 520. Motor drive base 520 is configured to advance and/or retract guide catheter actuating mechanism 502 in the direction indicated by arrow 526 by engagement with moveable base 524. In one embodiment, motor drive base 520 includes an actuator that moves guide catheter actuating mechanism 502 in the direction indicated by arrow 526. In one embodiment, as discussed above regarding FIG. 3A, guide catheter actuating mechanism 502 also includes a rotation actuator 506 configured to cause guide catheter 500 to rotate and a bend actuator 508 configured to cause the distal tip of guide catheter 500 to bend. As seen in FIG. 3B and FIG. 3C, movement of guide catheter actuating mechanism 502 in the direction indicated by arrow 526 will result in a corresponding axially movement of guide catheter 500. In the embodiment shown, guide catheter actuating mechanism 502 includes a housing 523. In this embodiment, both rotation actuator 506 and bend actuator 508 are located within housing 523 such that rotation actuator 506 and bend actuator 508 move along with the rest of guide catheter actuating mechanism 502 as it advances and retracts along motor drive base 520.

First leg 528 of Y-connector 510 is coupled to guide catheter actuating mechanism 502 via connector 516, and third leg 532 of Y-connector 510 is coupled to cassette 512 via connector 514. As shown in FIG. 3B and FIG. 3C, connector 516 is an axially fixed connection such that the axial position of Y-connector 510 relative to guide catheter actuating mechanism 502 is fixed. In this embodiment, because connector 516 is an axially fixed connection, movement of guide catheter actuating mechanism 502 in the direction indicated by arrow 526 will result in a corresponding axially movement of Y-connector 510. In this embodiment, connector 514 is an expandable and collapsible (e.g., telescoping) connector that expands and contracts in the direction indicated by arrow 526 as guide catheter actuating mechanism 502 and Y-connector 510 advance and retract. Thus, connector 514 ensures that third leg 532 of Y-connector 510 remains in communication with cassette 512 during advancement and refraction of guide catheter actuating mechanism 502. This provides a path for the percutaneous devices of cassette 512 to enter guide catheter 500 by passing through Y-connector 510 in all positions of guide catheter actuating mechanism 502.

While FIG. 3B and FIG. 3C show connector 514 as an expandable/collapsible element allowing for the relative axial motion between guide catheter actuating mechanism 502 and cassette 512, other suitable components may be expandable/collapsible elements instead of or in addition to connector

514. For example, in one embodiment, connector 516 may be expandable/collapsible such that connector 516 expands and collapses during advancement and retraction of guide catheter actuating mechanism 502. In this embodiment, Y-connector 510 remains fixed relative to cassette 512 and does not advance or retract with guide catheter actuating mechanism 502. In another embodiment, first leg 528 and/or third leg 532 may include expandable sections that expand and contract during advancement and retraction of guide catheter actuating mechanism 502.

In one embodiment, Y-connector 510 may be coupled to guide catheter actuating mechanism 502 and to guide catheter 500 such that Y-connector 510 does not rotate as guide catheter 500 is rotated by rotation actuator 506. For example, connector 516 may include a rotational bearing element such that guide catheter 500 is rotatable relative to Y-connector 510. In this embodiment, connector 516 also provides for a fluid seal between Y-connector 510 and guide catheter 500. In other embodiments, Y-connector 510 may be coupled to guide catheter actuating mechanism 502 and to guide catheter 500 such that Y-connector 510 does not move when the distal tip of guide catheter 500 is bent. In another embodiment, Y-connector 510 may be coupled to guide catheter actuating mechanism 502 and to guide catheter 500 such that Y-connector 510 rotates when guide catheter 500 is rotated. In this embodiment, connector 514 may include a rotational bearing element allowing Y-connector 510 to rotate relative to connector 514 and cassette 512.

In another embodiment, bedside system 12 includes an actuator, shown as Y-connector rotational actuator 522, that allows the user to control movement (e.g., advance, retract, rotate, etc.) of Y-connector 510 independent of the movement of guide catheter 500. In various embodiments, Y-connector rotational actuator 522 may be incorporated in the guide catheter actuating mechanism 502 or in the cassette 512. In one embodiment, controls 16 are configured to allow the user located within workstation 14 to control the movement of the Y-connector 510. In one embodiment, Y-connector 510 may be moved via Y-connector rotational actuator 522 to place Y-connector 510 in the proper position for insertion of the percutaneous devices of cassette 512 into third leg 532.

Figure 4:
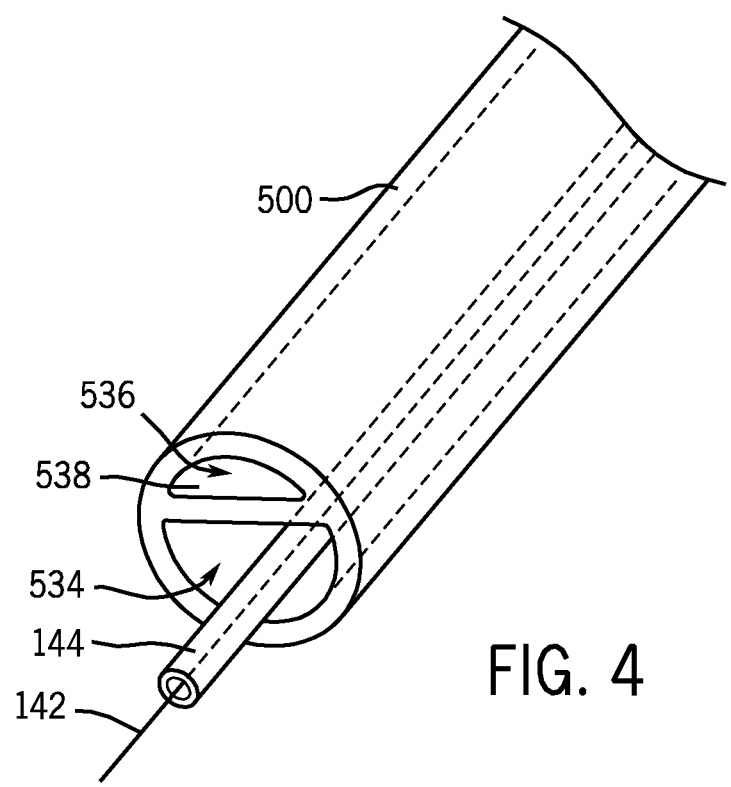
FIG. 4 is a perspective view of a guide catheter including a first lumen and a second lumen according to an exemplary embodiment.

In one embodiment of guide catheter 500 shown in FIG. 4, guide catheter 500 includes a first lumen 534 that runs the length of guide catheter 500 and a second internal lumen 536 that runs the length of guide catheter 500. First lumen 534 receives working catheter 144 and guide wire 142. As shown in FIG. 4, second lumen 536 includes a distal opening 538 located through the distal end of guide catheter 500. In other embodiments, distal opening 538 may be located through the sidewall of guide catheter 500 near or adjacent the distal tip of guide catheter 500. Second internal lumen 536 may be configured to allow fluid (e.g., contrast agent, medicine, etc.) to be delivered directly to the distal tip of guide catheter 500 without the need to introduce the fluid into first lumen 534 that contains the guide wire and/or working catheter. Second lumen 536 may provide for more accurate and precise delivery of fluids through guide catheter 500 that may allow the user to conserve (e.g., use less, etc.) contrast agent or medicine during a procedure. In this embodiment of guide catheter 500, second leg 530 of Y-connector 510 is in fluid communication with second lumen 536 and first leg 528 and third leg 532 of Y-connector 510 is in communication with first lumen 534.

Figure 5:
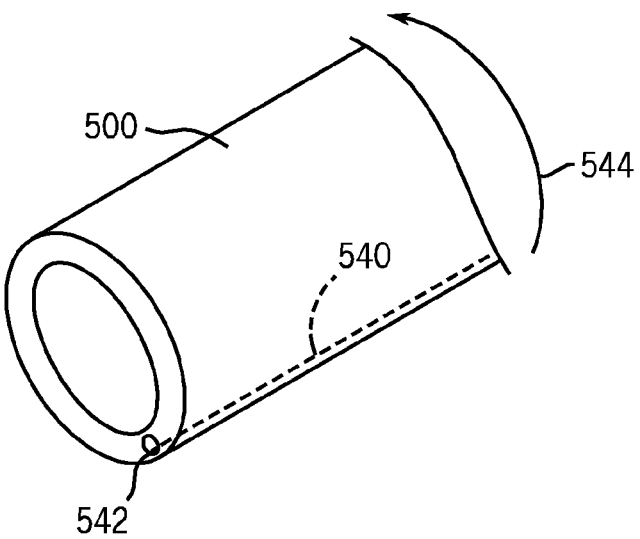
FIG. 5 is a perspective view of a guide catheter including a bend control element according to an exemplary embodiment.
Figure 6:
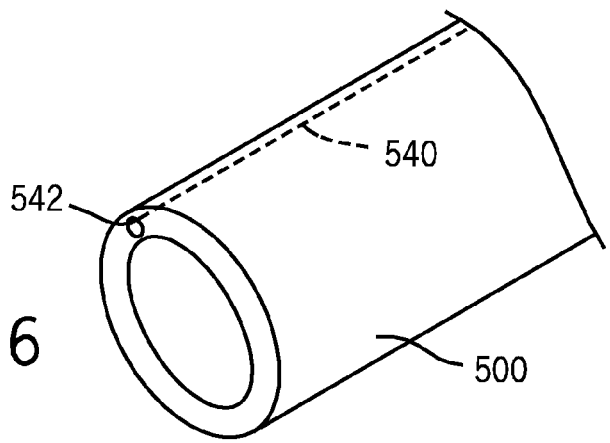
FIG. 6 is a perspective view of the guide catheter of FIG. 5 following axial rotation of the guide catheter.
Figure 7:
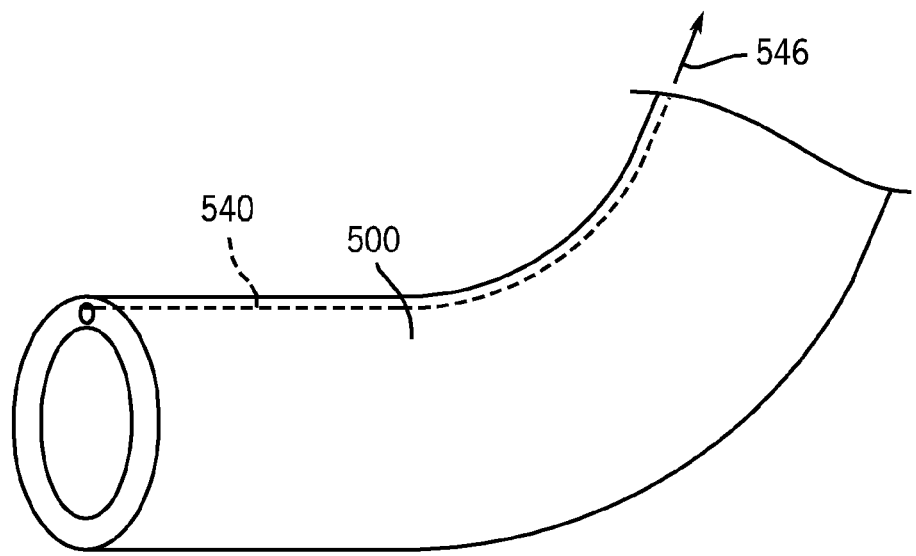
FIG. 7 is a perspective view of the guide catheter of FIG. 5 following bending of the distal tip of the guide catheter.

As shown in FIGS. 5-7, steerable guide catheter 500 includes one or more bend control elements that allows the user to cause bending of the distal tip of guide catheter 500. In FIGS. 5-7, the bend control element is shown as a control wire 540 that runs the length of guide catheter 500, and the distal end of control wire 540 is coupled to the distal end or tip of guide catheter 500 at attachment point 542. In this embodiment, the proximal end of control wire 540 is connected to bend actuator 508. In this embodiment, bend actuator 508 is configured to place tension on control wire 540 in response to the manipulation of controls 16 by the user. In this embodiment, bend actuator 508 includes one or more actuator to apply the tension to control wire 540.

As indicated by arrow 544, guide catheter 500 may be rotated to properly align the bend plane of guide catheter 500 as discussed below. As shown in FIG. 7, when tension, shown as arrow 546, is placed on control wire 540 the distal end or tip of the guide catheter 500 bends. In this embodiment, the greater the tension placed on control wire 540, the greater the degree of bending experienced in the distal tip of guide catheter 500. During a procedure, the user may bend the distal tip of the guide catheter 500 in order to accurately place the tip of the guide catheter into the intended location (e.g., into the ostium of either the left or right coronary artery) and/or to steer the guide catheter around curves in the patient's vascular system. The user is able to control the tension placed on control wire 540 via manipulation of controls 16 located remotely at workstation 14.

In another embodiment, guide catheter 500 includes a hydraulic bend control element instead of or in addition to the control wire. In this embodiment, the wall of the distal end of guide catheter 500 includes a bladder system. In this embodiment, bend actuator 508 is configured to control the fluid pressure within the bladder system in response to the user's manipulation of controls 16. In this embodiment, altering the fluid pressure within the bladder system causes the tip of guide catheter 500 to bend.

The degree of bending created in the tip of guide catheter 500 depends, in part, on the flexibility of the material of the guide catheter sidewall. For example, a guide catheter with a stiffer sidewall will bend less than a guide catheter with a more flexible sidewall when the same tension is applied via control wire 540. The flexibility of guide catheter 500 may be determined by the material and/or thickness of the guide catheter sidewall. The user may select a particular guide catheter 500 with a particular sidewall stiffness based upon the particular procedure that is being preformed.

In one embodiment, the flexibility of the distal tip of guide catheter 500 may be uniform along its length. In another embodiment, the flexibility of the distal tip of guide catheter 500 may be varied along its length. In this embodiment, the distal tip of guide catheter 500 will have a non-uniform bend response to the tension applied by the control wire. In one embodiment, the flexibility of the distal tip of the guide catheter 500 is varied by varying the thickness of the sidewall material of the guide catheter. The particular non-uniform bend response of a guide catheter may be selected based on the procedure to be preformed or based on the geometry of a particular patient's vascular system.

The bend control element of guide catheter 500 defines a bend plane of guide catheter 500. The bend plane is the plane in which the longitudinal axis of the bent portion of guide catheter 500 lies when guide catheter 500 is in the bent position. In various embodiments, the bend plane is tracked and information corresponding to the position of the bend plane relative to the patient's vascular system is displayed to the user located at the workstation 14. In one embodiment, the bend plane is tracked by monitoring the rotation of guide catheter 500 during a procedure. Rotation of guide catheter 500 may be tracked by encoders, resolvers, potentiometers, or any other position measuring device capable of detecting rotation. In another embodiment, the distal end of guide catheter 500 includes a relatively small permanent bend that lies in the bend plane. In one embodiment, the permanent bend in the distal end of guide catheter 500 is visible to the user during a procedure via real-time images of a patient's vascular system captured by imagining system 32. In another embodiment, the bend plane of guide catheter 500 may be marked via another landmark that is visible during imaging.

Figure 8:
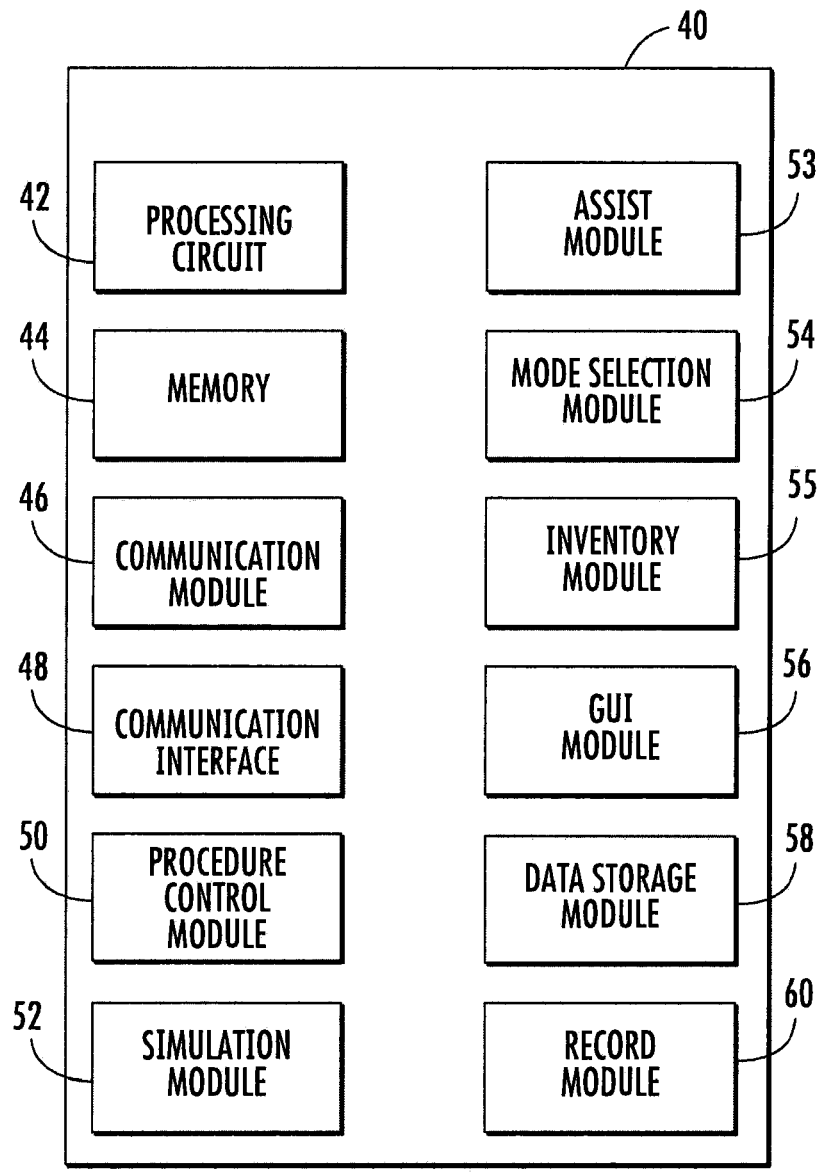
FIG. 8 is a block diagram of a controller for controlling a robotic catheter system according to an exemplary embodiment.

Referring to FIG. 8, a block diagram of controller 40 is shown according to an exemplary embodiment. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 42, memory 44, communication module or subsystem 46, communication interface 48, procedure control module or subsystem 50, simulation module or subsystem 52, assist control module or subsystem 53, mode selection module or subsystem 54, inventory module or subsystem 55, GUI module or subsystem 56, data storage module or subsystem 58, and record module or subsystem 60.

Processing circuit 42 may be a general purpose processor, an application specific processor (ASIC), a circuit containing one or more processing components, a group of distributed processing components, a group of distributed computers configured for processing, etc. configured provide the functionality of module or subsystem components 46, 50-60. Memory 44 (e.g., memory unit, memory device, storage device, etc.) may be one or more devices for storing data and/or computer code for completing and/or facilitating the various processes described in the present disclosure. Memory 44 may include volatile memory and/or non-volatile memory. Memory 44 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 44 is communicably connected to processing circuit 42 (e.g., via a circuit or any other wired, wireless, or network connection) and includes computer code for executing one or more processes described herein. A single memory unit may include a variety of individual memory devices, chips, disks, and/or other storage structures or systems.

Module or subsystem components 46, 50-60 may be computer code (e.g., object code, program code, compiled code, script code, executable code, or any combination thereof) for conducting each module's respective functions. Module components 46, 50-64 may be stored in memory 44, or in one or more local, distributed, and/or remote memory units configured to be in communication with processing circuit 42 or another suitable processing system.

Communication interface 48 includes one or more component for communicably coupling controller 40 to the other components of catheter procedure system 10 via communication links 38. Communication interface 48 may include one or more jacks or other hardware for physically coupling communication links 38 to controller 40, an analog to digital converter, a digital to analog converter, signal processing circuitry, and/or other suitable components. Communication interface 48 may include hardware configured to connect controller 40 with the other components of catheter procedure system 10 via wireless connections. Communication module 46 is configured to support the communication activities of controller 40 (e.g., negotiating connections, communication via standard or proprietary protocols, etc.).

Data storage module 58 is configured to support the storage and retrieval of information by controller 40. In one embodiment, data storage module 58 is a database for storing patient specific data, including image data. In another embodiment, data storage module 58 may be located on hospital network 34. Data storage module 58 and/or communication module 46 may also be configured to import and/or export patient specific data from hospital network 34 for use by controller 40.

Controller 40 also includes a procedure control module 50 configured to support the control of bedside system 12 during a catheter based medical procedure. Procedure control module 50 allows the manipulation of controls 16 by the user to operate bedside system 12. Procedure control module 50 may also cause data appropriate for a particular procedure to be displayed on monitors 26 and 28. Procedure control module 50 may include sets of instructions specific to various types of catheter based procedures that may be performed using bedside system 12. For example, procedure control module 50 may include one set of instructions that will be executed by processing circuit 42 if bedside system 12 is being used to perform a diagnostic catheterization procedure and another set of instructions that will be executed by processing circuit 42 if bedside system 12 is being used to perform a therapeutic catheter procedure. In one embodiment, procedure control module 50 includes instructions to control guide catheter actuating mechanism 502 to advance/retract, rotate, and bend guide catheter 500 as discussed above. In addition, procedure control module 50 may also be configured to allow a user located at workstation 14 to operate imaging system 32.

In one embodiment, bedside system 12 may be equipped with a variety (e.g., different types, makes, models, etc.) of steerable guide catheters each having a distal tip that is configured bend to a different predetermined shape or a different predetermined bend angle. In other embodiments, the distal tip of a single steerable guide catheter is configured to curve into a variety of different shapes or to a variety of different angles. As discussed above, controls 16 may include one or more controls or icons displayed on touch screen 18, that, when activated, causes the distal tip of the steerable guide catheter to bend to a particular shape or to a particular angle. In such embodiments, procedure control module 50 may be configured to send a control signal to guide catheter actuating mechanism 502 to cause guide catheter 500 to bend to the particular bend angle or the particular bend shape in response to a user's manipulation of controls 16. In addition, procedure control module 50 may be programmed with separate sets of instructions to be executed for different types (e.g., makes, models, sizes, bend characteristics, etc.) of guide catheters 500 that bedside system 12 may be equipped with.

In one embodiment, procedure control module 50 is programmed with instructions to cause the distal tip of guide catheter 500 to bend to a particular angle or to a particular shape when the user activates (e.g., touches) an icon on touch screen 18 related to the particular bend angle or shape. In one such embodiment, procedure control module 50 is programmed with instructions to allow the user to bend the distal tip of guide catheter 500 to any angle or shape within the range of motion of the particular guide catheter. In another embodiment, controller 40 is configured to identify (either automatically or via user input) the particular steerable guide catheter 500 equipped with bedside system 12 for a particular procedure. In this embodiment, procedure control module 50 may be configured to automatically identify the set of instructions to be executed to properly control guide catheter 500 via guide catheter actuating mechanism 502. In another such embodiment, procedure control module 50 may be configured to automatically cause icons to be displayed on touch screen 18 associated with the potential bend angles or bend shapes for the particular guide catheter 500 equipped with bedside system 12.

Controller 40 also includes simulation module or subsystem 52, assist module or subsystem 53, mode selection module or subsystem 54, inventory module or subsystem 55, GUI module or subsystem 56, data storage module or subsystem 58, and record module or subsystem 60. Generally, simulation module 52 is configured to run a simulated catheterization procedure based upon stored vascular image data and also based upon a user's manipulation of controls 16. Generally, assist module 53 is configured to provide information to the user located at workstation 14 during a real and/or simulated catheterization procedure to assist the user with the performance of the procedure. Specific embodiments of controller 40, including specific embodiments of simulation module 52, and assist module 53, are described in detail in International Application No. PCT/US2009/055318, filed Aug. 28, 2009, which is incorporated herein by reference in its entirety. Other specific embodiments of controller 40, including specific embodiments of GUI module 56, are described in International Application No. PCT/US2009/055320, filed Aug. 28, 2009, which is incorporated herein by reference in its entirety.

In one embodiment, simulation module 52 is configured to run a simulated catheterization procedure based upon stored vascular image data and also based upon a user's manipulation of controls 16. In this embodiment, simulation module 52 allows the user to run simulated procedures using various simulated steerable guide catheters. In this embodiment, the simulated procedure allows the user to practice a procedure before conducting a real procedure. In addition, the simulated procedure allows the user to practice a procedure with various types of steerable catheters to determine which steerable catheter is best suited for a particular type of procedure for the particular patient.

In one embodiment, assist module 53 is configured to provide information to the user during a real and/or simulated catheterization procedure to assist the user with the performance of the procedure. In one embodiment, assist module 53 may determine a particular type (e.g., size, shape, make, model, bend shape, bend response, etc.) of steerable guide catheter 500 that may be suitable for use in a particular procedure or for a particular patient and display the determined type of steerable guide catheter 500 to the user at workstation 14. In another embodiment, assist module 53 may automatically control bend actuator 508 to cause steerable guide catheter 500 to bend a proper amount for the performance of a particular procedure. For example, assist module 53 may determine, based on the images of a patient's heart, the amount of tension to apply to the control wire to cause steerable guide catheter 500 to bend into either the left or right ostium as needed for a particular procedure, and then assist module 53 may control guide catheter actuating mechanism 502 to apply the tension the control wire to cause steerable guide catheter 500 to bend into either the left or right ostium.

In one embodiment, guide catheter 500 may include one or more sensors, such as position sensor 501 (shown in FIG. 3A), that are configured to provide the three-dimensional position of the tip of guide catheter 500 relative to a patient's vascular system. In another embodiment, guide catheter 500 may include one or more sensors that provide the position of a percutaneous device (e.g., the guide wire and/or working catheter, etc.) relative to guide catheter 500. In various embodiments, position sensor 501 may be a magnetic or RF device configured to identify the location of the tip of guide catheter 500. In this embodiment, catheter procedure system 10 may include detectors appropriate for detecting the position of position sensor 501. In another embodiment, the three-dimensional position of the tip of the guide catheter relative to a patient's vascular system and/or the position of a percutaneous device (e.g., the guide wire and/or working catheter, etc.) relative to guide catheter 500 may be determined by appropriate image processing of images captured by imaging system 32.

In one embodiment, assist module 53 may be configured to control guide catheter actuating mechanism 502 to automatically rotate guide catheter 500 and/or bend the distal tip of guide catheter 500 into the proper position for a procedure. In one embodiment, the proper position may be determined automatically by controller 40 based upon the positional information from sensors and/or image data. In another embodiment, the user may input via controls 16 various position parameters (e.g., desired bend angle, position within heart to bend, etc.), and controller 40 may control guide catheter 500 via guide catheter actuating mechanism 502 to achieve the proper positioning. In another embodiment, assist module 53 may be configured to automatically advance one or more of the percutaneous devices (e.g., the guide wire and/or working catheter, etc.) within the guide catheter based upon the positional information from sensors and/or image data indicating the position of the percutaneous device relative to guide catheter 500. In various embodiments, automatic movement of guide catheter 500 or of other percutaneous devices under the control of assist module 53 may decrease procedure time, radiation dose from imaging system 32, and contrast agent dose that a patient receives.

Figure 9:
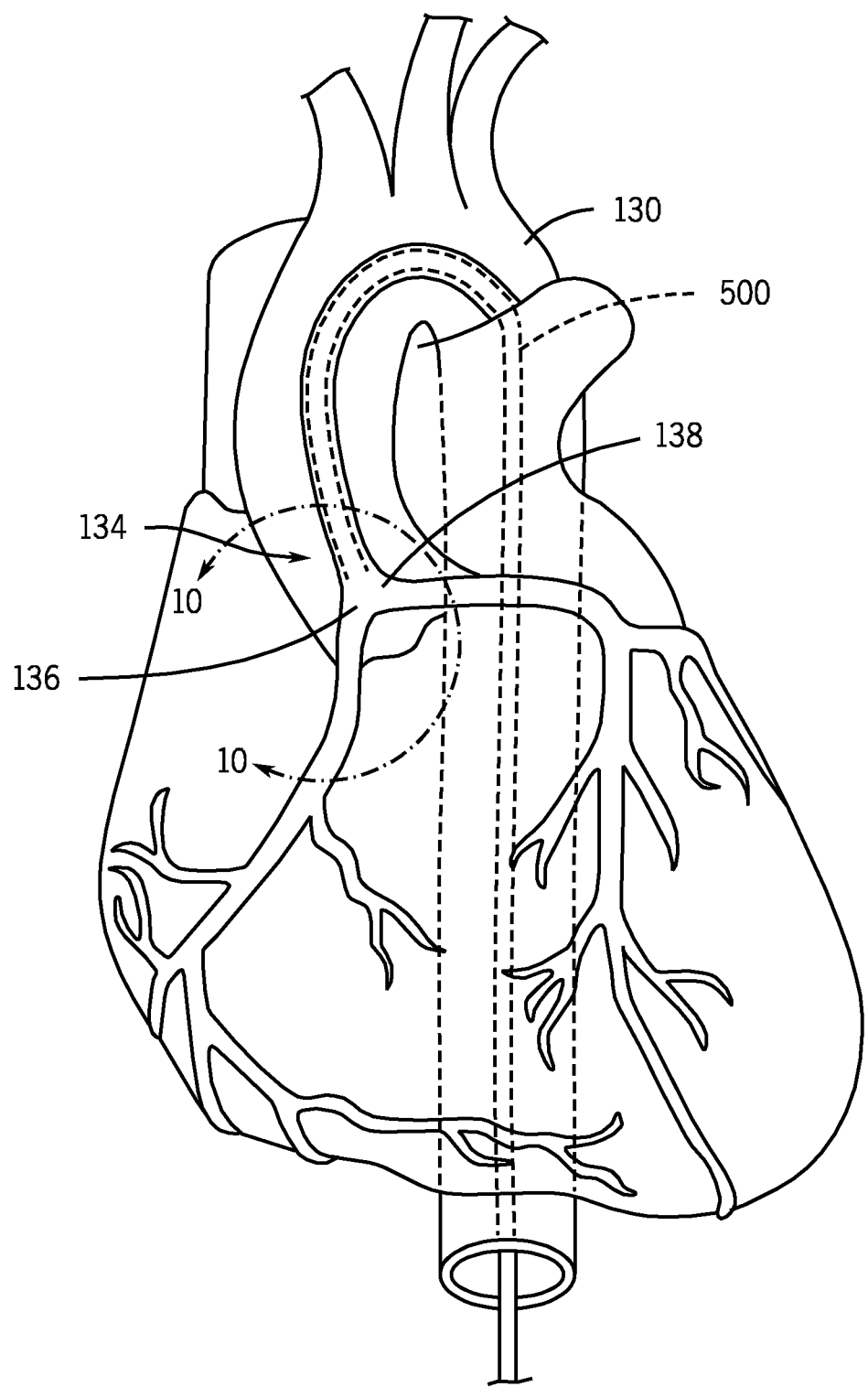
FIG. 9 is an image of a human heart shown during a catheterization procedure according to an exemplary embodiment.
Figure 10:
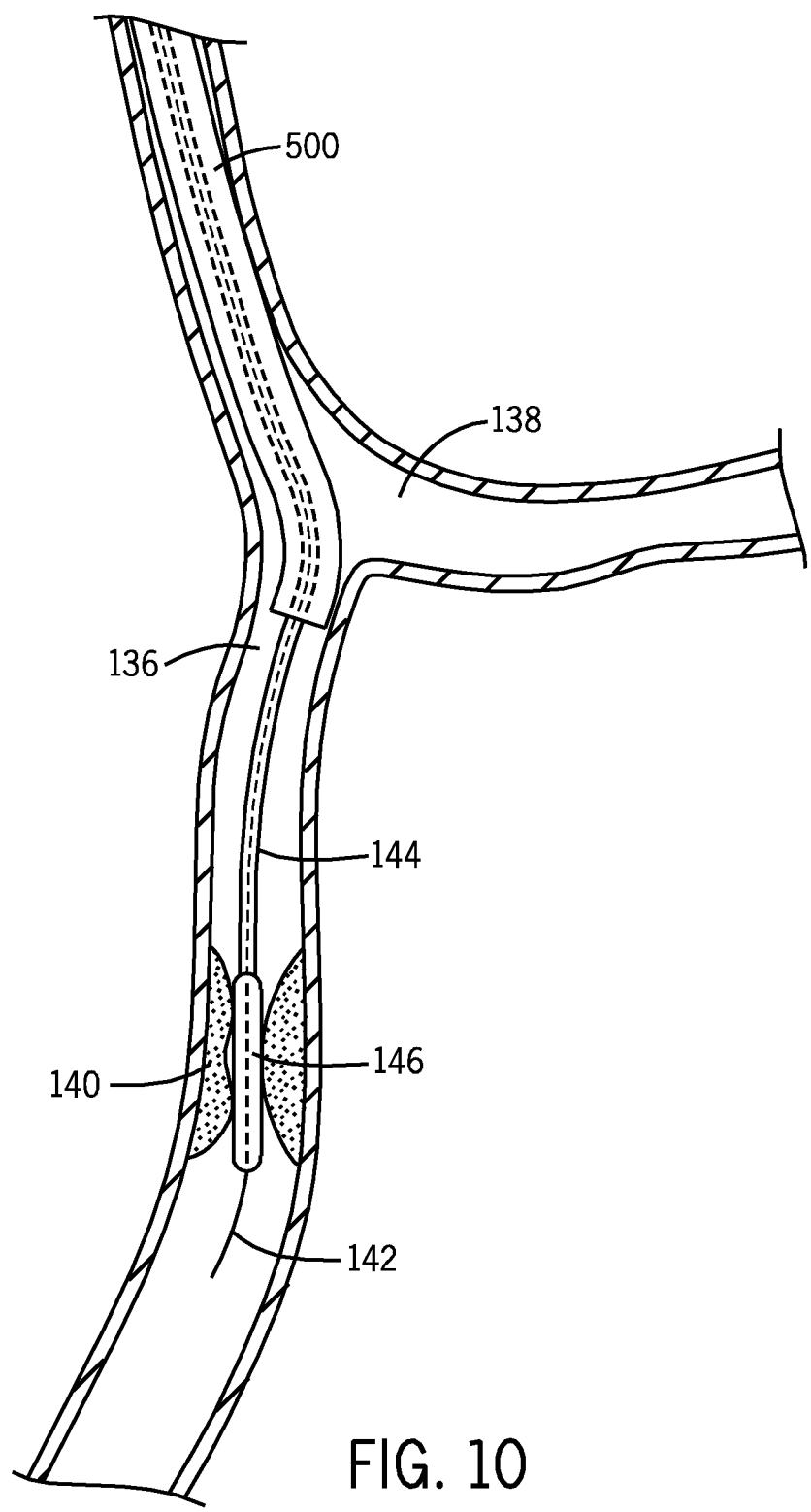
FIG. 10 is an image of coronary arteries shown during a catheterization procedure according to an exemplary embodiment.

Referring to FIG. 9 and FIG. 10, a human heart is shown during a catheterization procedure, shown as a balloon angioplasty procedure, utilizing steerable guide catheter 500. During the exemplary catheterization procedure shown, an incision is made, usually in the groin. A steerable guide catheter 500 is inserted through the incision into the femoral artery. Bedside system 12 is operated to advance steerable guide catheter 500 through the patient's arterial system, over the top of aortic arch 130, until steerable guide catheter 500 is positioned within coronary arteries 134 near the left ostium 136 and/or right ostium 138.

The distal end of steerable guide catheter 500 is bent via operation of bend actuator 508 to allow steerable guide catheter 500 to accurately navigate through the patient's arterial system. For example, the distal end of steerable guide catheter 500 may bent via operation of bend actuator 508 to steer guide catheter 500 around the aortic arch. In addition, distal end of steerable guide catheter 500 may bent via operation of bend actuator 508 to allow steerable guide catheter 500 to access either the left ostium 136 or the right ostium 138 of the aorta (access to the left ostium 136 is shown in FIG. 10). To navigate through a turn, such as the turn from the aorta into the left ostium 136, the user rotates guide catheter 500 to align the bend plane with the left ostium 136. The user then bends the distal end of guide catheter 500 so that the tip is pointing into the left ostium 136. Guide catheter 500 is then advanced axial to move guide catheter 500 into the left ostium 136.

Once guide catheter 500 is in place, bedside system 12 is operated to feed guide wire 142 through guide catheter 500 until guide wire 142 extends across lesion 140. Next, bedside system 12 is operated to advance working catheter 144 over guide wire 142 to position balloon 146 across lesion 140. Once working catheter 144 and balloon 146 are in place, balloon 146 is inflated to compress lesion 140 and to stretch the artery open thereby increasing blood flow to the heart. Balloon 146 is then deflated, guide catheter 500, guide wire 142 and working catheter 144 are removed, and the incision is closed.

During the procedure, contrast media may injected into the patient's heart through the steerable guide catheter 500 via the second leg of Y-connector 510. Imaging system 32 is then operated to capture images of the patient's heart and coronary arteries during the procedure. These images may be displayed to the user at workstation 14 to aid the user in positioning guide catheter 500, guide wire 142, and/or working catheter 144.

While the catheter based therapeutic procedure discussed above relates to a balloon angioplasty, it should be understood that the working catheter may be any type of catheter useful during the performance of any therapeutic procedure. For example, the catheter may include a stent that is expanded and left at the site of the lesion. Alternatively, the catheter may include structures adapted to cut or grind away the plaque forming the lesion.

The exemplary embodiments illustrated in the figures and described herein are offered by way of example only. Accordingly, the present application is not limited to a particular embodiment, but extends to various modifications that nevertheless fall within the scope of the appended claims.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. All such modifications are intended to be included within the scope of the present disclosure.

The order or sequence of any process or method steps may be varied or re-sequenced according to alternative embodiments. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Other substitutions, modifications, changes, and omissions may be made in the design, operating conditions and arrangement of the exemplary embodiments without departing from the scope of the present disclosure.

What is claimed is:

1. A catheter procedure system comprising:
    a user interface for receiving at least a first user input and a second user input;
    a guide catheter having a guide catheter shaft with a proximal end and a distal end;
    a guide catheter actuating mechanism including a rotation actuator coupled to the proximal end of the guide catheter, and an advance/retract actuator, the advance/retract actuator of the guide catheter actuating mechanism configured to advance and retract the guide catheter in response to the first user input and to rotate the proximal end of the guide catheter in response to the second user input;
    a Y-connector including a first leg, a second leg, and a third leg, each of the first leg, second leg and third leg having an internal lumen, each lumen being in communication with each other, the first leg being co-axial with the third leg and the second leg extending at an angle from the first leg, the internal lumen of the first leg being in communication with an internal lumen o the guide catheter; and
    a first connector coupling the Y-connector to the guide catheter actuating mechanism, wherein the first connector is configured to allow the Y-connector to advance and retract with the guide catheter and to allow the proximal end of the guide catheter to rotate without also causing the Y-connector to rotate, wherein at least a portion of the rotation actuator is between a portion of the first leg and a portion of the guide catheter.

2. The catheter procedure system of claim 1 wherein the guide catheter actuating mechanism includes a bend actuator that is configured to bend the distal tip of the guide catheter in response to a third user input received by the user interface.

3. The catheter procedure system of claim 2 wherein the user interface includes at least one control for receiving the third user input, the at least one control associated with a bend angle, and further wherein the guide catheter actuating mechanism is configured to bend the distal tip of the guide catheter to the bend angle in response to the third user input.

4. The catheter procedure system of claim 2 wherein the guide catheter includes a control element, and further wherein the guide catheter actuating mechanism bends the distal tip of the guide catheter via the control element.

5. The catheter procedure system of claim 4 wherein the control element is a control wire, and further wherein the guide catheter actuating mechanism applies tension to the control wire to bend the distal tip of the guide catheter.

6. The catheter procedure system of claim 1 further comprising:
    a cassette, the cassette including a guide wire actuator configured to advance and retract a guide wire, and a working catheter actuator configured to advance and retract a working catheter;
    wherein the guide catheter actuating mechanism is incorporated in the cassette.

7. The catheter procedure system of claim 6 wherein the Y-connector is moveable between a first position and a second position, wherein at least one of the guide wire and working catheter is inserted into the Y-connector after the Y-connector is moved to the first position.

8. The catheter procedure system of claim 1 further comprising a sensor configured to indicate the position of the distal tip of the guide catheter within a vascular system of a patient.

9. The catheter procedure system of claim 8 further comprising a control module configured to automatically move the guide catheter based upon the position indicated by the sensor.

10. The catheter procedure system of claim 8 wherein the guide catheter actuating mechanism includes a bend actuator that is configured to bend the distal tip of the guide catheter in response to a third user input received by the user interface.

11. The catheter procedure system of claim 1 wherein the position of the distal tip of the guide catheter within a vascular system of a patient is identified based upon image data.

12. The catheter procedure system of claim 11 further comprising a control module configured to automatically move the guide catheter based upon the position identified based upon the image data.

13. The catheter procedure system of claim 1 further comprising:
    a guide wire;
    a working catheter;

an actuator configured to advance and retract the guide wire and the working catheter; and a sensor configured to indicate the position of the distal tip of the guide catheter relative to the position of at least one of the guide wire and working catheter.

14. The catheter procedure system of claim 13 further comprising a control module configured to automatically advance at least one of the guide wire and working catheter based upon the position indicated by the sensor.

15. The catheter procedure system of claim 13 wherein the guide catheter actuating mechanism is configured to bend the distal tip of the guide catheter in response to a third user input received by the user interface.

16. The catheter procedure system of claim 1 wherein the guide catheter actuating mechanism is located within a lab unit and the user interface is located in a control room remote from the lab unit.

17. The catheter procedure system of claim 1 wherein the guide catheter actuating mechanism is part of a robotic catheter system.

18. The catheter procedure system of claim 1 further comprising a Y-connector actuator configured to move the Y-connector in response to a third user input received by the user interface.

19. The catheter procedure system of claim 1 wherein the guide catheter includes a first lumen and a second lumen, wherein the first lumen is configured to receive a percutaneous device and the second lumen is configured to receive a fluid.

20. The catheter procedure system of claim 19 wherein the fluid is a contrast agent.

21. The catheter procedure system of claim 19 wherein the fluid is medication.

22. The catheter procedure system of claim 19 wherein the second lumen includes a distal opening adjacent the distal tip of the guide catheter allowing fluid to be delivered directly to the distal tip of the guide catheter.

23. The catheter procedure system of claim 1 further comprising:

a cassette, the cassette including a guide wire actuator configured to advance and retract a guide wire, and a working catheter actuator configured to advance and retract a working catheter;

a second connector coupling the Y-connector to the cassette;

wherein the Y-connector, the first connector and the second connector are configured such that the guide wire and the working catheter are allowed to be advanced from the cassette through the second connector into the Y-connector and then through the first connector and then into a lumen of the guide catheter.

24. The catheter procedure system of claim 23 further comprising:

a base;

wherein the guide catheter actuating mechanism is supported by the base and translates relative to the base to advance and retract the guide catheter; and further wherein the Y-connector translates relative to the base during advancement and retraction of the guide catheter.

25. The catheter procedure system of claim 24 wherein the guide catheter actuating mechanism includes a housing and a rotation actuator supported by the housing, wherein the rotation actuator is configured to impart rotation to the guide catheter, and further wherein the rotation actuator translates relative to the base during advancement and retraction of the guide catheter.

26. The catheter procedure system of claim 24 wherein the second connector expands and collapses during translation of the Y-connector relative to the base.

27. The catheter procedure system of claim 24 wherein the base is a motor drive base including at least one actuator to impart movement to the guide catheter actuating mechanism resulting in advancement and retraction of the guide catheter.

* * * * *